United States Patent [19]
Williams et al.

[11] Patent Number: 5,224,373
[45] Date of Patent: Jul. 6, 1993

[54] FLEXIBLE HUMIDITY INDICATOR AND CONTAINER

[76] Inventors: Christi A. Williams; Joseph M. Williams, both of 5019 Forest Nook Ct., Houston, Tex. 77018

[21] Appl. No.: 699,312
[22] Filed: May 9, 1991
[51] Int. Cl.$^5$ ............................................. G01W 1/00
[52] U.S. Cl. ................................. 73/29.02; 73/29.04
[58] Field of Search ..................... 73/335, 29.04, 29.02

[56] References Cited

U.S. PATENT DOCUMENTS

| | | | |
|---|---|---|---|
| 2,249,867 | 7/1941 | Snelling | 73/335.08 |
| 2,716,338 | 8/1955 | Blinn | 73/335.01 X |
| 2,815,662 | 12/1957 | Thomas | 73/29.02 |
| 2,934,954 | 5/1960 | Phillips | 374/142 |
| 3,425,388 | 2/1969 | West | 73/335.07 |
| 4,034,609 | 7/1977 | Fuller | 73/335.01 |
| 4,150,570 | 4/1979 | Fuller | 73/335.01 |

FOREIGN PATENT DOCUMENTS 892214  3/1962  United Kingdom ................. 73/335

Primary Examiner—Hezron E. Williams
Assistant Examiner—Joseph W. Roskos
Attorney, Agent, or Firm—Kenneth A. Roddy

[57] ABSTRACT

A thin flexible humidity sensor and indicator of sandwich construction sealably mounted in an opening in the wall of a container provides a visual indication of the humidity within the container. The humidity sensor and indicator has an intermediate layer of flexible humidity sensitive material chemically treated to change color corresponding to exposure to predetermined levels of humidity, a thin flexible layer of transparent water vapor barrier material on one side, and a thin flexible layer of water vapor permeable material on its opposite side which are sealed together and sealably secured over the opening in the container wall. The water vapor permeable layer is disposed on the interior of the container and provides communication between the container interior and the humidity sensitive layer and the transparent water vapor barrier layer and the humidity sensitive layer are visible from the exterior of the container to provide a visual indication of the value of the humidity within the container. In a preferred embodiment, the humidity sensitive vehicle is a sheet of blotter paper treated with a chemical solution of cobalt chloride and additives and the water vapor permeable material is flash spun, film fibril high density polyethylene material which prevents lint and debris from the blotter paper from entering the interior of the container and prevents direct contact between the chemically treated blotter paper and the contents of the container.

22 Claims, 1 Drawing Sheet

FLEXIBLE HUMIDITY INDICATOR AND CONTAINER

BACKGROUND OF THE INVENTION

1. Field of the Invention

This invention relates generally to humidity indicators for containers, and more particularly to a thin flexible color change humidity indicator of sandwich construction installed in the side wall of a flexible container.

2. Brief Description of the Prior Art

Thin flexible water vapor barrier containers, such as envelopes, bags, and packages are commonly used in the electronics industry to store and ship moisture sensitive electronic components. Such containers, with the moisture sensitive components enclosed therein, are usually stacked in storage bins or boxes. They are also shipped to various destinations through the mail or via commercial carriers and the container and its delicate contents are subjected to rough handling often in high humidity environments.

Often, moisture sensitive elements, such as electronic components, are damaged due to exposure to humidity through damaged packaging or improper packaging. Many electronic components can also be contaminated by particulate debris which can enter through a damaged package or which can even be caused by particulate matter of the package itself.

Therefore, it would be desirable to provide a thin flexible, humidity indicator suitable for use in the wall of a flexible water vapor barrier container which will visually indicate varying levels of humidity within the container and has a particulate filter between the humidity responsive element in the indicator and the contents of the container and which will allow stacking of flexible containers for shipping and storage without damage or contamination of the contents.

Dehydrated packaging was developed during the second World War to protect metallic, organic, and synthetic materials from deterioration due to high relative humidity in the Pacific and the tropics, and was improved by placing a predetermined amount of an indicating desiccant silica gel inside the package which would indicate an unsafe condition. However, once the silica gel showed an unsafe condition, it could only be used again if it was reconditioned (by heat or otherwise).

Color change chemical indicators were developed after the war which used blotting paper coated with various solutions of cobalt chloride and additives. The blotting paper/cobalt chloride indicators were placed inside the container and some containers were provided with a window so that the indicator could be seen without opening the container.

There are currently two basic forms of humidity indicators in the art which are suggested to be mounted in the walls of product packaging: a relatively expensive reusable type, and a relatively inexpensive disposable type. Conventional reusable types of humidity indicators consist of a rigid metal or plastic plug having a visual indicator and window in the head of the plug which is installed in the wall of the container. These plug type indicators may be used in both flexible and rigid containers.

Humidial Corporation of Colton, Calif. manufactures a disposable blotting paper/cobalt chloride indicator card which is placed inside of a container, and also a reusable rigid metal or plastic plug which has a window and a blotting paper indicator card installed in the face of the plug. The window type rigid plug indicator is a hollow bolt-like configuration having a threaded shaft and may be installed on flexible or rigid containers using hand tools and a gasket and locknut.

West, U.S. Pat. No. 3,425,388 discloses a disposable rigid window plug type humidity indicator which can be installed in either rigid or flexible plastic containers. West teaches a rigid plastic cup-like inner member having a flange on the bottom end and a peripheral bead at the top end, a transparent plastic cup-like outer member which snap fits onto the inner member, and a humidity responsive color change element which is clamped therebetween. The inner member flange is heat sealed to the package interior and its upper end extends through an opening in the package. The transparent outer member serves as a sight window and the inner member has an opening to the inside of the container to provide free communication between the container interior and the humidity responsive element.

Each of the above described humidity indicators present problems when used on flexible water vapor barrier containers and packages whether they be plastic or fiber and particularly in their use with flexible water vapor barrier bags of the type used in the electronics industry to store and ship moisture sensitive electronic components.

Due to the rigidity and thickness inherent in the design of the above described rigid humidity indicators when they are installed in a flexible container they will deform the container outward and add thickness and bulk to the area of the container at which they are installed. The rigidity of the inner fastener members can damage components inside the container. Should the flexible containers be stacked for storage or shipment, the cumulative weight and thickness of the indicators could seriously deform and/or displace the contents of the flexible container.

The opening in the inner member of the above mentioned indicators is intended to provide free communication between the contents of the container and the humidity responsive element and there is no provision of a particulate barrier between the humidity responsive element and the contents. Thus, there exists the possibility of particulate contamination of the contents from the humidity responsive element, which is composed of blotting paper. Blotting paper sheds paper fibers and lint. Also, the blotting paper contains a chemical solution of cobalt chloride and additives which will cause chemical contamination and/or corrosion of the contents should they come in contact with the indicating element itself.

Chemically treated blotting paper cards have been placed inside sealed opaque packages or containers, but this method also presents the problem of contamination of the contents by chemicals and debris from the card and requires that the package or container be cut open for inspection and then resealed.

The present invention is distinguished over the prior art in general, and the West patent in particular, by a thin flexible humidity sensor and indicator of sandwich construction sealably mounted in an opening in the wall of a container which provides a visual indication of the humidity within the container. The present humidity sensor and indicator has an intermediate layer of flexible humidity sensitive material chemically treated to change color corresponding to exposure to predetermined levels of humidity, a thin flexible layer of transparent water vapor barrier material on one side, and a thin flexible layer of water vapor permeable material on its opposite side which are sealed together and sealably secured over the opening in the container wall. The water vapor permeable layer is disposed on the interior of the container and provides communication between the container interior and the humidity sensitive layer and the transparent water vapor barrier layer and the humidity sensitive layer are visible from the exterior of the container to provide a visual indication of the value of the humidity within the container. In a preferred embodiment, the humidity sensitive vehicle is a sheet of blotter paper treated with a chemical solution of cobalt chloride and additives and the water vapor permeable material is flash spun, film fibril high density polyethylene material which prevents lint and debris from the blotter paper from entering the interior of the container and prevents direct contact between the chemically treated blotter paper and the contents of the container.

SUMMARY OF THE INVENTION

It is therefore an object of this invention to provide a humidity indicator to be installed in the wall of a container and which will allow direct reading, by an outside observer, of the humidity inside the container.

It is another object of this invention to provide a humidity indicator that is thin, lightweight and flexible and suitable for installation in flexible water vapor barrier containers because it conforms to irregular content shapes.

Another object of this invention to provide a humidity indicator that is thin, lightweight and flexible and allows stacking of flexible water vapor barrier containers without damage, distortion, or misalignment of the contents.

Another object of this invention to provide a humidity indicator that prevents contact between the humidity responsive element and the contents of the container and prevents particulate debris from the humidity responsive element from entering the container.

Another object of this invention is to provide a disposable humidity indicator that is simple in construction, inexpensive to manufacture, and is durable and reliable in use.

Another object of this invention is to provide a water vapor barrier container having a humidity indicator in its side wall which is particularly useful for storing and shipping moisture sensitive materials and which will visually indicate varying levels of humidity within the container.

A further object of this invention is to provide a flexible water vapor barrier container with a humidity indicator in its side wall which allows the container to conform to the shape of the contents and can be stacked without damage, distortion or misalignment of the contents.

A still further object of this invention is to provide a flexible water vapor barrier container with a humidity indicator in its side wall and with a particulate filter between the humidity responsive element to prevent contamination of the contents from fibers of the indicator material and prevent direct contact of the contents with the chemicals in the indicator.

Other objects of the invention will become apparent from time to time throughout the specification and claims as hereinafter related.

The above noted objects and other objects of the invention are accomplished by a thin flexible humidity sensor and indicator of sandwich construction sealably mounted in an opening in the wall of a container which provides a visual indication of the humidity within the container. The humidity sensor and indicator has an intermediate layer of flexible humidity sensitive material chemically treated to change color corresponding to exposure to predetermined levels of humidity, a thin flexible layer of transparent water vapor barrier material on one side, and a thin flexible layer of water vapor permeable material on its opposite side which are sealed together and sealably secured over the opening in the container wall. The water vapor permeable layer is disposed on the interior of the container and provides communication between the container interior and the humidity sensitive layer and the transparent water vapor barrier layer and the humidity sensitive layer are visible from the exterior of the container to provide a visual indication of the value of the humidity within the container. In a preferred embodiment, the humidity sensitive vehicle is a sheet of blotter paper treated with a chemical solution of cobalt chloride and additives and the water vapor permeable material is flash spun, film fibril high density polyethylene material which prevents lint and debris from the blotter paper from entering the interior of the container and prevents direct contact between the chemically treated blotter paper and the contents of the container.

DESCRIPTION OF THE PREFERRED EMBODIMENT

Figure 1:
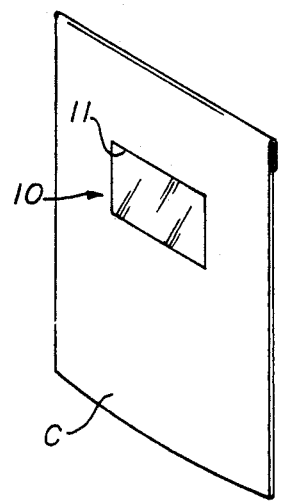
FIG. 1 is an isometric view of a flexible bag or envelope type container having a humidity indicator in accordance with the present invention installed thereon.
Figure 3:
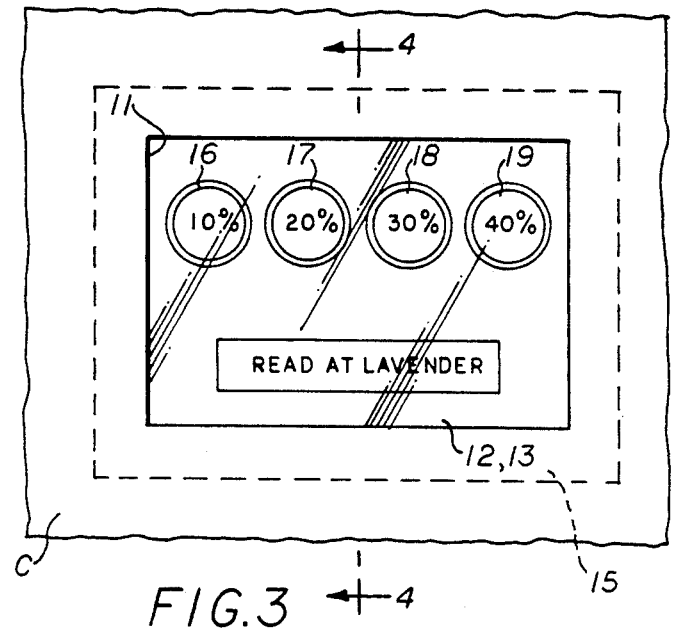
FIG. 3 is an elevation view of the humidity indicator in the assembled condition installed on a portion of a flexible container.
Figure 2:
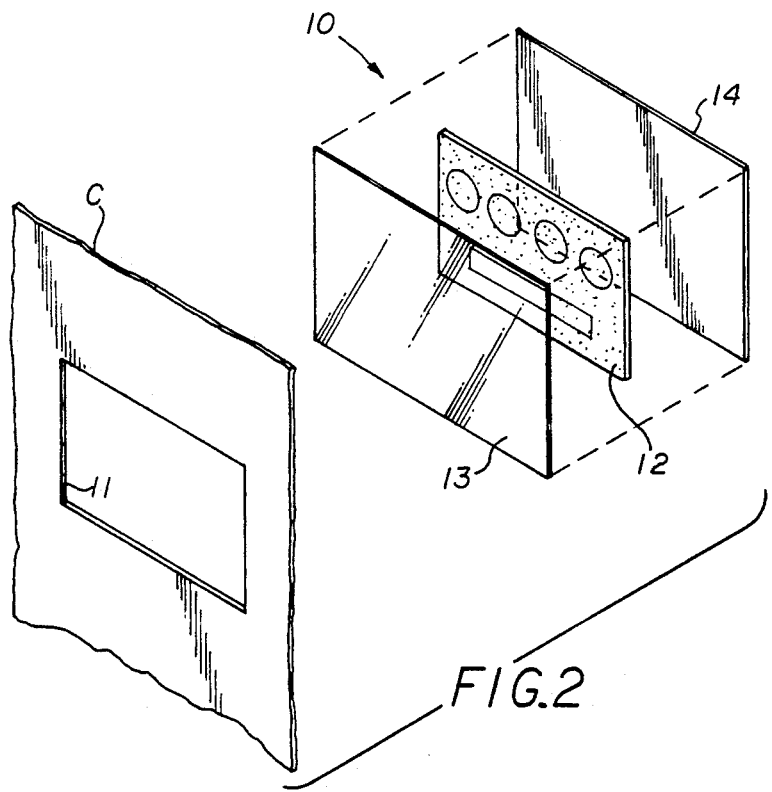
FIG. 2 is an exploded isometric view of the humidity indicator in an unassembled condition.
Figure 4:
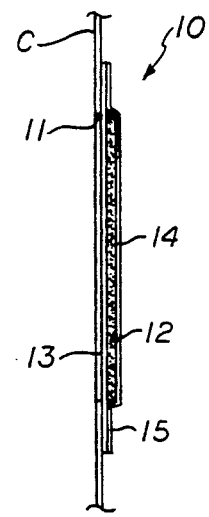
FIG. 4 is a cross section of the humidity indicator taken along line 4—4 of FIG. 3.

Referring to the drawings by numerals of reference, there is shown in FIG. 1, a flexible bag or envelope type container C having a humidity sensor and indicator 10 installed thereon. Referring additionally to FIGS. 2-4, the container C is formed of thin flexible plastic or fiber water vapor barrier material. The container C is provided with a rectangular opening 11 through one side wall which serves as a mounting opening for the humidity indicator 10.

A preferred water vapor barrier material for the container is suggested to be formed of a flash spun, film fibril sheet of high density polyethylene, such as Tyvek (tm, E. I. DuPont de Nemours & Co.) with a coating or layer of aluminum and perhaps another layer of low density polyethylene film, such as manufactured by Richmond Technology, Inc., Redlands, Calif. Another commercially available material suitable for the container is Marvelguard ECIA (tm, Ludlow Corporation, Homer, La.).

The humidity sensor and indicator 10 is a sandwich construction having a thin intermediate layer 12 of flexible humidity sensitive material chemically treated to change color responsive to exposure to predetermined levels of humidity, a thin flexible outer layer 13 of transparent water vapor barrier film material on one side, and a thin flexible inner layer 14 of water vapor permeable material on its opposite side which are sealed together. The inner layer 14 is the layer which will reside on the inner surface of the container.

The flexible outer film layer 13 is formed of a single sheet of flexible, transparent plastic film material having a low water vapor transmission rate. The flexible inner layer 14 is formed of a single sheet of flash spun, film fibril high density polyethylene material, such as Tyvek (tm, E. I. DuPont de Nemours & Co.) having a high moisture vapor transmission rate. The inner layer 14 also serves as a chemical and particulate filter, as described hereinafter. The intermediate layer 12 is formed of a single sheet of moisture absorbent material such as blotter paper treated with a chemical solution of cobalt chloride and additives which will change color at different levels of humidity.

The transparent flexible outer layer 13 of plastic film and the inner layer 14 of flash spun, film fibril high density polyethylene material are rectangular configurations having an outer periphery larger than the rectangular opening 11 in the container C. The intermediate layer 12 of treated blotter paper is also a rectangular configuration, but its outer periphery is approximately the same size as the opening 11 in the container C and smaller than the outer periphery of the layers 13 and 14.

The intermediate layer 12 is sandwiched between the outer layer 13 and inner layer 14 and the layers are heat sealed together or otherwise sealably connected by conventional methods to form a single unitary flexible structure. The intermediate layer 12, being smaller than the outer layer 13 and inner layer 14 defines a surrounding peripheral edge 15 formed of only the layers 13 and 14 which serves as a mounting edge for mounting the assembled unit onto the container.

Thus, when the layers are sealed together, a unitary flexible humidity indicator 10 is formed which has an outer transparent water vapor barrier, an intermediate humidity responsive element, and an inner water vapor permeable layer in direct contact with the humidity responsive element and which serves as a chemical and particulate filter.

The preferred intermediate layer of blotter paper 12 is provided with suitable indicia on its outer surface representing different levels of humidity, such as a series of laterally spaced circles 16, 17, 18, and 19 bearing the numerals "10%", "20%", "30%", and "40%", respectively, indicating percentages of relative humidity. The cobalt chloride solution is impregnated in each of the circular areas such that when the humidity is below a predetermined level at a predetermined temperature, all of the circles are blue and as the relative humidity increases, the circle areas will change color from a blue color (dry) through a lavender color to a pink color (humid). As the relative humidity decreases they will reversibly change from a pink color (humid) through a lavender color to a blue color (dry). In other words, each circular area 16-19 responds to a relative humidity condition denoted by the percentage value shown in the circular area, by changing color. For example, if the relative humidity level rises to 20%, circular area 17 turns to the lavender color, etc. The indicia and colors are clearly observable through the transparent outer layer 13.

Although cobalt chloride solutions are no more harmful to humans than common table salt, they are known to cause corrosion of some metals if direct contact occurs. Also, blotter paper is known to shed paper fibers and lint. However, in the present invention, the inner layer 14 being formed of flash spun, film fibril high density polyethylene material will allow water vapor to be transmitted to the intermediate layer of blotter paper 12 while at the same time will prevent direct contact between the contents of the container and the chemically treated blotter paper and will prevent any paper fibers or lint from entering the interior of the container.

The assembled humidity indicator 10 is installed on the container C by placing it against the interior of the side wall of the container with the intermediate layer 12 aligned with the container opening 11 and the peripheral edge 15 surrounding and overlapping the opening and then heat sealing or otherwise sealably securing the humidity indicator over the opening by conventional methods.

Once the humidity indicator 10 has been sealed over the opening 11, it becomes an integral part of the container side wall. Thus, a flexible container is provided which has at least one side wall having a humidity indicator portion. The humidity indicator portion having a transparent water vapor barrier on the exterior through which a humidity responsive element is visible and a moisture vapor permeable section on its inner surface which serves as a chemical and particulate filter. Such a container allows one to quickly and easily determine the relative humidity within the interior of the container by merely looking at the exterior of the container. Because the humidity indicator is thin and flexible, such containers can be easily stored in a stacked condition and can be shipped without damage to the contents caused by the humidity indicator. Also because of its inexpensive construction, the package, including the humidity indicator, can be discarded after use.

While this invention has been described fully and completely with special emphasis upon a preferred embodiment, it should be understood that within the scope of the appended claims the invention may be practiced otherwise than as specifically described herein.

What is claimed is:

1. A flexible humidity sensor and indicator of sandwich construction to be sealably mounted in an opening in the wall of a sealable container to provide a visual indication from the exterior of the container of the humidity within the container when sealed comprising;

a first thin flexible layer of transparent material, a second intermediate layer of flexible humidity sensitive material chemically treated to visually indicate the value of humidity to which it is exposed, and a third thin flexible layer of water vapor permeable material of sufficient density to be permeable to humid gases and impermeable to particulate matter, said first, second, and third layers sealed together to form a unitary flexible construction having an intermediate layer of humidity sensitive material with a transparent layer on one side and a water vapor permeable layer on an opposite side thereof and said first and said third layers having an outer periphery extending beyond the outer periphery of said intermediate layer to define a mounting edge surrounding said intermediate layer which is adapted to be sealably secured over the opening in the wall of the container to be supported thereon with said second intermediate layer disposed within the opening, such that at least a portion of said water vapor permeable layer is disposed on the interior of the container to provide humidity communication between the container interior and said humidity sensitive layer and to serve as a chemical and particulate filter to prevent contamination of articles in the container, and said transparent layer and said intermediate humidity sensitive layer are visible from the exterior of the container to provide a visual indication of the value of the humidity to which said intermediate humidity sensitive layer is exposed.

2. A humidity sensor and indicator according to claim 1 in which
said second intermediate layer of humidity sensitive material is formed of moisture absorbent material chemically treated to change color when exposed to a predetermined level of humidity.

3. A humidity sensor and indicator according to claim 2 in which
said moisture absorbent material bears indicia on its surface representative of differing levels of relative humidity and the area at which the indicia is borne is treated with differing chemical solutions such that when the relative humidity to which the absorbent material is exposed is below a predetermined level at a predetermined temperature, all of the indicia are of a first color and as the relative humidity increases, the areas bearing the indicia will change in variable gradients of colors responsive to a relative humidity condition corresponding to the indicia and the change occur in the reverse order as the relative humidity decreases.

4. A humidity sensor and indicator according to claim 2 in which
said moisture absorbent material comprises a sheet of blotter paper.

5. A humidity sensor and indicator according to claim 2 in which
said moisture absorbent material is treated with a chemical solution including cobalt chloride which will reversibly change color responsive to exposure to predetermined levels of humidity.

6. A humidity sensor and indicator according to claim 1 in which
said first thin flexible layer of transparent material is formed of a sheet of transparent plastic film having a low water vapor transmission rate to serve as a water vapor barrier between the exterior of the container and said second intermediate humidity sensitive layer.

7. A humidity sensor and indicator of sandwich construction to be sealably mounted in an opening in the wall of a container to provide a visual indication from the exterior of the container of the humidity within the container comprising;
a first thin flexible layer of transparent material,
a second intermediate layer of flexible humidity sensitive material chemically treated to visually indicate the value of humidity to which it is exposed, and
a third thin flexible layer of water vapor permeable material formed of a sheet of flash spun, film fibril high density polyethylene material having a high water vapor transmission rate and being of sufficient density to allow humidity communication therethrough,
said first, second, and third layers sealed together to form a unitary flexible construction having an intermediate layer of humidity sensitive material with a transparent layer on one side and a water vapor permeable layer on an opposite side thereof and said first and said third layers having an outer periphery extending beyond the outer periphery of said intermediate layer to define a mounting edge surrounding said intermediate layer which is adapted to be sealably secured over the opening in the wall of the container to be supported thereon with said second intermediate layer disposed within the opening, such that
at least a portion of said water vapor permeable layer is disposed on the interior of the container to provide humidity communication between the container interior and said humidity sensitive layer and to serve as a chemical and particulate filter, and said transparent layer and said intermediate humidity sensitive layer are visible from the exterior of the container to provide a visual indication of the value of the humidity to which said intermediate humidity sensitive layer is exposed.

8. A humidity sensor and indicator according to claim 1 in which
said first thin flexible layer of transparent material is formed of a sheet of transparent plastic film having a low water vapor transmission rate to serve as a water vapor barrier between the exterior of the container and said second intermediate humidity sensitive layer,
said second intermediate layer of humidity sensitive material is formed of moisture absorbent material chemically treated to change color when exposed to a predetermined level of humidity, and
said third thin flexible layer of water vapor permeable material is formed of a sheet of flash spun, film fibril high density polyethylene material having a high water vapor transmission rate.

9. A humidity sensor and indicator according to claim 8 in which
said moisture absorbent material comprises a sheet of blotter paper treated with a chemical solution including cobalt chloride which will reversibly change color responsive to exposure to predetermined levels of humidity, and
said third thin flexible layer of water vapor permeable material is formed of a sheet of flash spun, film fibril high density polyethylene material having a high water vapor transmission rate and of sufficient density to prevent lint and debris from said blotter paper from entering the interior of the container and prevent direct contact between said chemically treated blotter paper and the contents of the container.

10. A humidity sensor and indicator according to claim 9 in which
said first, second, and third layers are heat sealed together to form a unitary construction and said first layer of transparent film material is capable of being heat sealed to the surface of the container.

11. A humidity sensing and indicating container having visual indicating means for indicating from the exterior of the container the humidity within the container comprising;
a container formed of material having a low water vapor transmission rate having at least one side wall formed of flexible material with an opening therethrough,
a thin flexible humidity sensor and indicator sealably mounted in said opening to provide a visual indication from the exterior of the container of the humidity within the container, said humidity sensor and indicator having a first thin flexible layer of transparent material, a second intermediate layer of flexible humidity sensitive material chemically treated to visually indicate the value of humidity to which it is exposed, and a third thin flexible layer of water vapor permeable material of sufficient density to be permeable to humid gases and impermeable to particulate matter, said first, second, and third layers sealed together to form a unitary sandwich construction having an intermediate layer of humidity sensitive material with a transparent layer on one side and a water vapor permeable layer on an opposite side thereof and sealably secured over the opening in said container side wall, such that the interior surface of said container side wall has a portion of said water vapor permeable material exposed to provide humidity communication between said container interior and said humidity sensitive layer and said transparent layer and said humidity sensitive layer are visible from the exterior of said container to provide a visual indication of the value of the humidity to which said humidity sensitive layer is exposed.

12. A container according to claim 11 in which
said second intermediate layer of humidity sensitive material is formed of moisture absorbent material chemically treated to change color when exposed to a predetermined level of humidity at a predetermined temperature.

13. A container according to claim 12 in which
said moisture absorbent material bears indicia on its surface representative of differing levels of humidity and the area at which the indicia is borne is treated with differing chemical solutions such that when the relative humidity to which the absorbent material is exposed is below a predetermined level, all of the indicia are of a first color and as the relative humidity increases, the areas bearing the indicia will change in variable gradients of colors responsive to a relative humidity condition corresponding to the indicia and the change occurs in the reverse order as the relative humidity decreases.

14. A container according to claim 12 in which
said moisture absorbent material comprises a sheet of blotter paper.

15. A container according to claim 12 in which
said moisture absorbent material is treated with a chemical solution including cobalt chloride which will reversibly change color responsive to exposure to predetermined levels of humidity.

16. A container according to claim 11 in which
said first thin flexible layer of transparent material is formed of a sheet of transparent plastic film having a low water vapor transmission rate to serve as a water vapor barrier between the exterior of said container and said second intermediate humidity sensitive layer.

17. A container according to claim 11 in which
said third thin flexible layer of water vapor permeable material is formed of a sheet of flash spun, film fibril high density polyethylene material having a high water vapor transmission rate.

18. A container according to claim 11 in which
said first thin flexible layer of transparent material is formed of a sheet of transparent plastic film having a low water vapor transmission rate to serve as a water vapor barrier between the exterior of said container and said second intermediate humidity sensitive layer, said second intermediate layer of humidity sensitive material is formed of moisture absorbent material chemically treated to change color when exposed to a predetermined level of humidity, said third thin flexible layer of water vapor permeable material is formed of a sheet of flash spun, film fibril high density polyethylene material having a high water vapor transmission rate, and said first, second, and third layers are heat sealed together to form a unitary flexible construction and sealed to the surface of said container side wall over said opening.

19. A container according to claim 18 in which
said moisture absorbent material comprises a sheet of blotter paper treated with a chemical solution including cobalt chloride which will reversibly change color responsive to exposure to predetermined levels of humidity, and said third thin flexible layer of water vapor permeable material is formed of a sheet of flash spun, film fibril high density polyethylene material having a high water vapor transmission rate and of sufficient density to prevent passage of lint and debris from said blotter paper from entering the interior of said container and prevent direct contact between said chemically treated blotter paper and the contents of said container.

20. A container according to claim 11 in which
said container is comprised of flash spun, film fibril high density polyethylene material having a layer of aluminum on one side.

21. A container according to claim 11 in which
said container is comprised of a sheet of flash spun, film fibril high density polyethylene material having a layer of aluminum and a layer of plastic water vapor impervious film.

22. A container according to claim 11 in which
said container is comprised of a sheet of material having a layer of aluminum and a layer of plastic film.

* * * * *